(12) United States Patent
Collier

(10) Patent No.: US 10,462,992 B2
(45) Date of Patent: Nov. 5, 2019

(54) HYBRID TOMATO VARIETY H1418

(71) Applicant: H.J. Heinz Company Brands LLC, Pittsburgh, PA (US)

(72) Inventor: George Collier, Wheatley (CA)

(73) Assignee: H.J. Heinz Company Brands LLC, Pittsburgh, PA (US)

( * ) Notice: Subject to any disclaimer, the term of this patent is extended or adjusted under 35 U.S.C. 154(b) by 6 days.

(21) Appl. No.: 15/855,051

(22) Filed: Dec. 27, 2017

(65) Prior Publication Data

US 2018/0116150 A1    May 3, 2018

Related U.S. Application Data

(63) Continuation of application No. 15/227,906, filed on Aug. 3, 2016.

(60) Provisional application No. 62/201,499, filed on Aug. 5, 2015.

(51) Int. Cl.
*A01H 5/08* (2018.01)
*A01H 1/00* (2006.01)
*A01H 6/82* (2018.01)

(52) U.S. Cl.
CPC ............... *A01H 5/08* (2013.01); *A01H 6/825* (2018.05)

(58) Field of Classification Search
None
See application file for complete search history.

(56) References Cited

U.S. PATENT DOCUMENTS

2013/0312131 A1* 11/2013 Bunn ............... A01G 22/00
800/260

* cited by examiner

*Primary Examiner* — Phuong T Bui
(74) *Attorney, Agent, or Firm* — Fitch, Even, Tabin & Flannery LLP

(57) ABSTRACT

Hybrid tomato variety 'H1418' is described. The 'H1418' tomato variety is a ground-culture hybrid tomato variety suitable for machine harvest.

11 Claims, 1 Drawing Sheet
(1 of 1 Drawing Sheet(s) Filed in Color)

HYBRID TOMATO VARIETY H1418

CROSS REFERENCE TO RELATED APPLICATIONS

This application is a continuation of U.S. application Ser. No. 15/227,906, filed Aug. 3, 2016, now U.S. Pat. No. 10,238,048, which claims the benefit of U.S. Provisional Application No. 62/201,499, filed Aug. 5, 2015, both of which are hereby incorporated by reference in their entireties.

FIELD

This invention relates to the field of plant breeding. In particular, this invention relates to a new tomato, *Solanum lycopersicum*, variety denominated 'H1418'.

BACKGROUND

Breeding improved tomato varieties involves providing genetics that give an advantage to the grower, processor, consumer, or other member of the supply chain. The improvement may be in the form of field performance, disease resistance, factory performance, or a fruit quality characteristic. For a tomato variety to be suitable to be grown for processing, the variety must have a concentrated fruit setting and maturity, firm fruit, and sufficient rot tolerance to allow early fruit to remain rot-free while later fruit continues to develop and ripen.

Most commercial processing tomato varieties are hybrids resulting from a cross pollination of two true-breeding, inbred parents. Through the use of true-breeding lines, a hybrid is produced that often displays characteristics of each parent, and often demonstrates characteristics that are superior to either parent alone, or that allow a hybrid to mask inadequacies of the individual parents.

Processing tomato varieties combining high levels of tolerance to bacterial canker (*Clavibacter michiganense* ssp. *michiganense*), early blight (*Alternaria solani*), and bacterial spot (*Xanthomonas* spp.) are highly desirable in humid climates where these diseases present production issues.

Moreover, tomato varieties adapted to arid climates, combining resistance to tomato spotted wilt virus (TSWV) and race 3 of *Fusarium oxysporum* f. sp. *lycopersici*, are desirable to the processing industry in California and other global tomato processing regions where these disease limit production. Additionally, tomato varieties adapted to arid climates that combine resistance to TSWV with high levels of soluble solids (° Brix), thin viscosity, and strong yields are also highly desirable for the California processing industry.

Further, *Fusarium oxysporum* f. sp. *lycopersici* race 3 (*Fusarium* 3) is a growing problem in the California tomato growing region and in other production areas worldwide, such as the Dominican Republic and Mexico. Productive, adapted varieties have been in demand by growers and processors since the mid 1990's with resistance to this pathogen. The disease has become a major limiting factor in tomato production in some California fields. Growers and processors need a range of tomato varieties with *Fusarium* 3 resistance, since products specifications vary in regards to juice viscosity, soluble solids content, field storage, and general field adaptability.

An additional important contribution that tomatoes provide to the human diet is the antioxidant lycopene. Specifically, processing tomato varieties are the key form of tomato intake in the US diet. Higher levels of lycopene are beneficial both from a nutritional standpoint and from a consumer perception and quality standpoint. Tomato varieties having higher levels of lycopene result in products with a deeper red color that can be considered an indicator of higher product quality. Thus, a tomato variety with higher levels of lycopene can be valuable from both a nutritional standpoint and a quality standpoint. However, to be commercially viable and useful, the tomato variety must perform acceptably as required by any other processing tomato variety. Previous varieties with increased lycopene levels have shown severe reductions in fruit quality, firmness, yield, and a sensitivity to fruit rots.

SUMMARY

In order to meet these needs, the present invention provides improved tomato variety 'H1418'.

In particular, the present invention provides improved tomato variety 'H1418', which has resistance to early blight, bacterial spot, and bacterial canker diseases of tomato coupled with superior rot resistance and comparative field yield to industry standard varieties such as 'H3402' and 'H9706'. The 'H1418' variety has resistance to verticillium race 1, *Fusarium* races 1 and 2, southern root knot nematode, bacterial speck race 0, bacterial canker, bacterial spot, and early blight. The fruit of 'H1418' are medium size, have good color and an average fruit weight of 74 grams. Tolerance to fruit rot in 'H1418' is excellent, allowing for once-over machine harvesting applications requiring extended field holding.

The characteristics that determine the quality of tomato fruit used for processing are different from that of tomato fruit used for the fresh market. Processing characteristics are commonly tested on samples of tomato pulp or juice produced in a way that is well known in the art. For example, a fixed mass of tomatoes may be cooked in a microwave oven for several minutes to halt any enzymatic breakdown of the sample, lost water is replaced, and the sample is pulped to remove skin and seeds to produce a uniform juice sample. The juice sample can be analyzed for various quality parameters important to processing tomato including, but not limited to, gross viscosity measurements such as juice Bostwick, soluble solids measurements using a refractometer (° Brix), measurements of acidity and pH, and measurements of color via a Hunter a/b score. The Hunter a/b score is an international industry and USDA standard color measurement of tomato products that provides a representation of the color of the product in a single dimensionless unit. The "a" value represents color on the green to red dimension whereas "b" represents the blue to yellow dimension; a higher a/b ratio is associated with more red color and is often considered a superior product.

Tomato varieties contain varying levels of lycopene (Garcia and Barrett, 2006). Lycopene content of tomato juice can be measured using a protocol developed by Anthon and Barrett (2001), which involves an ethanol/hexane extraction followed by quantification using reflectance at 503 nm.

As used herein, tomato variety 'H1418', tomato plant 'H1418', tomato seed 'H1418', and 'H1418' all refer to the hybrid tomato variety 'H1418', and parts and seeds thereof, having ATCC Accession Number PTA-124121.

Accordingly, in one embodiment, the present invention is directed to tomato seed designated as 'H1418' having ATCC Accession Number PTA-124121. In another embodiment, the present invention is directed to a tomato plant and parts isolated therefrom produced by growing 'H1418' tomato seed. In yet another embodiment, the present invention is directed to a tomato plant and parts isolated therefrom having all the physiological and morphological characteristics of a tomato plant produced by growing 'H1418' tomato seed having ATCC Accession Number PTA-124121. In still another embodiment, the present invention is directed to an Fi hybrid tomato seed, plants grown from the seed, and leaves, ovules, pollen, fruit, cotyledons, embryos, meristems, anthers, roots, root tips, pistils, flowers, stems, calli, stalks, hypocotyls, and pericarps isolated therefrom having 'H1418' as a parent, wherein 'H1418' is grown from 'H1418' tomato seed having ATCC Accession Number PTA-124121.

Tomato plant parts include leaves, ovules, pollen, fruit, cotyledons, embryos, meristems, anthers, roots, root tips, pistils, flowers, stems, calli, stalks, hypocotyls, pericarps, and the like. In another embodiment, the present invention is further directed to tomato fruit, stems, leaves, parts of leaves, roots, root tips, pollen, ovules, and flowers isolated from 'H1418' tomato plants. In another embodiment, the present invention is further directed to tissue culture or cells derived from 'H1418' tomato plants.

In yet another embodiment, the present invention is further directed to a method of selecting tomato plants by a) growing 'H1418' tomato plants wherein the 'H1418' plants are grown from tomato seed having ATCC Accession Number PTA-124121; and b) selecting a plant from step a). In another embodiment, the present invention is further directed to tomato plants, plant parts and seeds produced by the tomato plants, where the tomato plants are isolated by the selection method of the invention.

In another embodiment, the present invention is further directed to a method of breeding tomato plants by crossing a tomato plant with a plant grown from 'H1418' tomato seed having ATCC Accession Number PTA-124121. In still another embodiment, the present invention is further directed to tomato plants, tomato parts from the tomato plants, and seeds produced therefrom where the tomato plant is isolated by the breeding method of the invention.

BRIEF DESCRIPTION OF THE DRAWING

The patent or application file contains at least one drawing executed in color. Copies of this patent or patent application publication with color drawings will be provided by the Office upon request and payment of the necessary fee.

The FIGURE illustrates fruit and general plant structure of tomato variety 'H1418'.

DETAILED DESCRIPTION

Described herein is a new and distinct tomato variety named 'H1418' that was developed to provide a ground-culture hybrid tomato variety (i.e., not grown on stakes) that is suitable for machine harvest, and is adaptable to the humid climactic conditions of regions such as Michigan, USA; Ohio, USA; Indiana, USA; Pennsylvania, USA; and southern Ontario, Canada.

Plants of the tomato variety 'H1418' are resistant to verticillium wilt race 1, *Fusarium* races 1 and 2, root knot nematode, bacterial speck race 0, early blight, bacterial spot, and bacterial canker. Additionally, plants of the tomato variety 'H1418' have a large sprawling vine size compared to other tomato varieties of the same market class and very high yield potential. Fruit from the tomato variety 'H1418' is medium sized and has good color compared to other tomato varieties of the same market class. Moreover, the tomato variety 'H1418' is adapted to culture in humid growing regions such as the eastern United States and southern Ontario Canada.

Stability of the 'H1418' Tomato Variety

The variety is uniform and stable within commercially acceptable limits. As is true with other tomato varieties, a small percentage of variants can occur within commercially acceptable limits for almost any characteristic during the course of repeated multiplication. However, no variants were observed during the two years in which the variety was observed to be uniform and stable.

Characterization of the 'H1418' Tomato Variety
Seedling
Anthocyanin in hypocotyl of 2-15 cm seedling: Present
Habit of 3-4 week old seedling: Normal
Mature Plant
Growth: Determinate
Form: Normal
Size of canopy: Large
Habit: Semi-erect
Stem
Branching: Profuse (e.g., 'UC 82')
Branching at cotyledonary or first leafy node: Present
Number of nodes below first inflorescence: 7-10
Number of nodes between early (1st-2nd, 2nd-3rd) inflorescences: 1-2
Number of nodes between later developing inflorescences: 1-2
Pubescence on younger: Sparsely hairy (scattered long hairs)
Leaf (Mature Leaf Beneath the 3rd Inflorescence)
Type: Tomato
Morphology of mature leaf: Compound with major and some minor leaflets
Margins of major leaflets: Nearly entire
Marginal rolling or wiltiness: Absent
Surface of major leaflets: Rugose (bumpy or veiny)
Pubescence: Smooth
Inflorescence (Observations from 3rd Inflorescence)
Type: Simple
Average number of flowers in inflorescence: 7
Leafy or "running" inflorescences: Absent
Flower
Calyx: Normal, lobes awl-shaped
Calyx-lobes: Shorter the corolla
Corolla color: Yellow
Style pubescence: Sparse
Anthers: All fused into tube
Fasciation (1st flower of 2nd or 3rd inflorescence): Absent
Fruit (3rd Fruit of 2nd or 3rd Cluster)
Typical fruit shape: Blocky, with hip
Shape of transverse section: Round
Shape of stem end: Flat
Shape of blossom end: Indented (slight)
Shape of pistil scar: Dot
Abscission layer: Absent (jointless)
Point of detachment of fruit at harvest: At calyx attachment
Average length (in mm) of mature fruit (stem axis): 66.5 mm
Average diameter (in mm) of fruit at widest point: 42.5 mm
Average weight (in g) of mature fruit: 74 g
Number of locules: Two
Fruit surface: Slightly rough
Fruit base color (mature-green stage): Apple or medium green
Fruit pattern (mature-green stage): Uniform green
Fruit color, full-ripe: Red
Flesh color full-ripe: Red/Crimson Flesh color: With lighter and darker areas in walls
Locular gel color of table-ripe fruit: Red
Ripening: Uniform
Stem scar size: Small (e.g., 'Roma')
Core: Present
Epidermis color: Yellow
Epidermis: Normal
Epidermis texture: Average
Thickness of the pericarp: 5.6 mm
Disease and Pest Reaction
Disease and Pest Reaction: Resistant to verticillium wilt, race 1, *Fusarium* races 1 and 2, root knot nematode, bacterial speck, race 0, early blight, bacterial spot, and bacterial canker
Chemistry and Composition of Full-Ripe Fruits

TABLE 1

|  | Variety 'H1418' | Check Variety 'H9553' | Check Variety 'H3402' |
| --- | --- | --- | --- |
| Soluble solids as °Brix | 5.29 | 4.77 | 5.17 |
| Juice Bostwick | 11.7 | 12.4 | 12.2 |

Fruiting season: Medium (e.g., 'Westover')
Relative maturity in areas tested: Medium
Adaptation
Culture: Field
Principle use(s): Concentrated products
Machine harvest: Adapted
Regions to which adaptation has been demonstrated: Northeastern USA Further Embodiments Additional methods include, without limitation, chasing selfs. Chasing selfs involves identifying inbred plants among tomato plants that have been grown from hybrid tomato seed. Once the seed is planted, the inbred plants may be identified and selected due to their decreased vigor relative to the hybrid plants that grow from the hybrid seed, or by enzymatic or DNA patterns. By locating the inbred plants, isolating them from the rest of the plants, and self-pollinating them (i.e., "chasing selfs"), a breeder can obtain an inbred line that is identical to an inbred parent used to produce the hybrid.

Accordingly, another aspect of the present invention relates to a method for producing an inbred tomato variety by: planting seed of the tomato variety 'H1418'; growing plants from the seed; identifying one or more inbred tomato plants; controlling pollination in a manner which preserves homozygosity of the one or more inbred plants; and harvesting resultant seed from the one or more inbred plants. The step of identifying the one or more inbred tomato plants may further include identifying plants with decreased vigor, i.e., plants that appear less robust than plants of the tomato variety 'H1418'. Tomato plants capable of expressing substantially all of the physiological and morphological characteristics of the parental inbred lines of tomato variety 'H1418' include tomato plants obtained by chasing selfs from seed of tomato variety 'H1418'.

One of ordinary skill in the art will recognize that once a breeder has obtained inbred tomato plants by chasing selfs from seed of tomato variety 'H1418', the breeder can then produce new inbred plants such as by sib-pollinating, or by crossing one of the identified inbred tomato plant with a plant of the tomato variety 'H1418'.

DEPOSIT INFORMATION

Tomato Variety 'H1418'

A deposit of tomato variety 'H1418' is maintained by HeinzSeed Company, having an address at 6755 C. E. Dixon, Stockton, Calif. 95206, United States of America. Access to the deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of variety 'H1418' will be irrevocably removed by affording access to a deposit of at least 2,500 seeds of the variety with the American Type Culture Collection, (ATCC), ATCC Patent Depository, 10801 University Boulevard, Manassas, Va., 20110, USA.

At least 2,500 seeds of tomato variety 'H1418' were deposited on Apr. 18, 2017 according to the Budapest Treaty in the American Type Culture Collection (ATCC), ATCC Patent Depository, 10801 University Boulevard, Manassas, Va., 20110, USA. The deposit has been assigned ATCC number PTA-124121. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed.

The deposit will be maintained in the ATCC depository, which is a public depository, for a period of 30 years, or 5 years after the most recent request, or for the effective life of the patent, whichever is longer, and will be replaced if the deposit becomes nonviable during that period.

The invention claimed is:

1. Tomato seed designated as 'H1418', representative sample of seed having been deposited under ATCC Accession Number PTA-124121.

2. A plant produced by growing the seed of claim 1.

3. A plant part from the plant of claim 2, wherein the part is selected from the group consisting of leaves, ovules, pollen, fruit, cotyledons, meristems, anthers, roots, root tips, pistils, flowers, stems, calli, stalks, hypocotyls, pericarps, and combinations thereof.

4. A plant part from the plant of claim 2, wherein said part is a tomato fruit.

5. A tomato plant having all the physiological and morphological characteristics of the tomato plant of claim 2.

6. A plant part from the plant of claim 5, wherein the part is selected from the group consisting of leaves, ovules, pollen, fruit, cotyledons, meristems, anthers, roots, root tips, pistils, flowers, stems, calli, stalks, hypocotyls, pericarps, and combinations thereof.

7. A plant part from the plant of claim 5, wherein said part is a tomato fruit.

8. Pollen of the plant of claim 2.

9. An ovule of the plant of claim 2.

10. A tissue culture of the plant of claim 2.

11. A method of making tomato seeds, said method comprising crossing the plant of claim 2 with another tomato plant and harvesting seeds therefrom.

* * * * *